United States Patent
Nelson (10) Patent No.: US 11,857,213 B2
(45) Date of Patent: Jan. 2, 2024

(54) FORCEPS WITH HINGED JAWS AND FORCE DISTRIBUTION

(71) Applicant: GYRUS ACMI, INC., Westborough, MA (US)

(72) Inventor: Jeffrey J. Nelson, Plymouth, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 177 days.

(21) Appl. No.: 17/341,876

(22) Filed: Jun. 8, 2021

(65) Prior Publication Data

US 2022/0061873 A1 Mar. 3, 2022

Related U.S. Application Data

(60) Provisional application No. 63/071,415, filed on Aug. 28, 2020.

(51) Int. Cl.
*A61B 17/28* (2006.01)
*A61B 17/00* (2006.01)
*A61B 17/29* (2006.01)

(52) U.S. Cl.
CPC .. *A61B 17/282* (2013.01); *A61B 2017/00367* (2013.01); *A61B 2017/2932* (2013.01); *A61B 2017/2933* (2013.01)

(58) Field of Classification Search
CPC .......... A61B 17/282; A61B 17/29; A61B 2017/00367; A61B 2017/2933; A61B 2017/2825; A61B 2017/2936; A61B 2017/2937; A61B 18/1442; A61B 2018/00577; A61B 2018/00589; A61B 2018/00607; A61B 2018/0063
See application file for complete search history.

(56) References Cited

U.S. PATENT DOCUMENTS 5,735,849 A * 4/1998 Baden ................ A61B 18/1442
606/205
6,773,438 B1 8/2004 Knodel
7,491,202 B2 2/2009 Odom et al.
(Continued)

FOREIGN PATENT DOCUMENTS

EP 0623316 A1 11/1994
EP 2127604 A1 12/2009

OTHER PUBLICATIONS

"United Kingdom Application Serial No. 2111619.9, Search Report dated Dec. 3, 2021", 4 pgs.

*Primary Examiner* — Shaun L David
*Assistant Examiner* — Rachael L Geiger
(74) *Attorney, Agent, or Firm* — Schwegman Lundberg & Woessner, P.A.

(57) ABSTRACT

A surgical forceps can include a first shaft, a cam feature, a first jaw, a second jaw, an actuator arm, and a second shaft. The cam feature can be connected to the first shaft. The first jaw can define a cam interface and an actuator track. The cam interface can be engaged with the cam feature, and the first jaw can be movable between an open position and a closed position. The first jaw can be movable relative to the second jaw. The actuator arm can include a distal portion configured to apply a closing force on the first jaw when the first jaw is moved out of the open position. The second shaft can move the cam interface along the cam feature to move the first jaw between the open position and the closed position.

19 Claims, 6 Drawing Sheets

(56) References Cited

U.S. PATENT DOCUMENTS

| | | |
|---|---|---|
| 8,858,588 B2 * | 10/2014 | Sigmon, Jr. ............ A61B 17/08 |
| | | 606/205 |
| 2003/0114850 A1 | 6/2003 | Mcclurken et al. |
| 2005/0101991 A1 | 5/2005 | Ahlberg et al. |
| 2010/0010512 A1 * | 1/2010 | Taylor ................ A61B 17/0491 |
| | | 606/144 |
| 2010/0137854 A1 | 6/2010 | Hosier |
| 2011/0306968 A1 | 12/2011 | Beckman et al. |
| 2012/0016391 A1 | 1/2012 | Aguirre et al. |
| 2012/0059375 A1 | 3/2012 | Couture et al. |
| 2012/0071871 A1 | 3/2012 | Lue et al. |
| 2017/0348043 A1 | 12/2017 | Wang et al. |
| 2017/0348044 A1 | 12/2017 | Wang et al. |
| 2019/0015124 A1 | 1/2019 | Williams et al. |

* cited by examiner

FORCEPS WITH HINGED JAWS AND FORCE DISTRIBUTION

CLAIM OF PRIORITY

This patent application claims the benefit of priority, under 35 U.S.C. Section 119(e), to Jeffrey Nelson U.S. Patent Application Ser. No. 63/071,415, entitled "FORCEPS WITH HINGED JAWS AND FORCE DISTRIBUTION," filed on Aug. 28, 2021, which is hereby incorporated by reference herein in its entirety.

BACKGROUND

Medical devices for diagnosis and treatment, such as forceps, are often used for medical procedures such as laparoscopic and open surgeries. Forceps can be used to manipulate, engage, grasp, or otherwise affect an anatomical feature, such as a vessel or other tissue of a patient during the procedure. Forceps often include an end effector that is manipulatable from a handle of the forceps. For example, jaws located at a distal end of a forceps can be actuated via elements of the handle between open and closed positions to thereby engage the vessel or other tissue. Forceps can include an extendable and retractable blade that can be extended distally between the jaws to lacerate tissue. The handle can also be capable of supplying an input energy, such as electromagnetic energy or ultrasound, to the end effector for sealing of the vessel or tissue during the procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Electrosurgical forceps often include a pivoting mechanism allowing jaws of the forceps to move between open and closed positions. In some examples, frames of the jaws can be driven, such as by a shaft, using a camming mechanism to move between the open and closed positions. Often the camming features of the jaws are positioned at or near a proximal end of the jaw frames to allow the jaws to wide enough to receive tissue therein. Because the camming features are located at a proximal portion of the jaws (often proximal of a pivot point of the jaws), a distal portion of the jaws can exert a lower clamping force than a proximal portion of the jaws. That is, a clamping or closing force applied by the jaws has a distribution as the jaws extend proximally to distally.

The present disclosure can help to address these issues by including one or more actuator arms connected to one or more shafts of the forceps and engaged with the jaws, respectively. Each actuator arm can be configured to apply a force on a first jaw towards the second jaw and a force on the second jaw towards the first jaw. The forces can be applied to a portion of the jaw that is distal of the pivot point, helping to increase the closing force at medial and distal portions of the jaws.

The above discussion is intended to provide an overview of subject matter of the present patent application. It is not intended to provide an exclusive or exhaustive explanation of the invention. The description below is included to provide further information about the present patent application.

Figure 1:
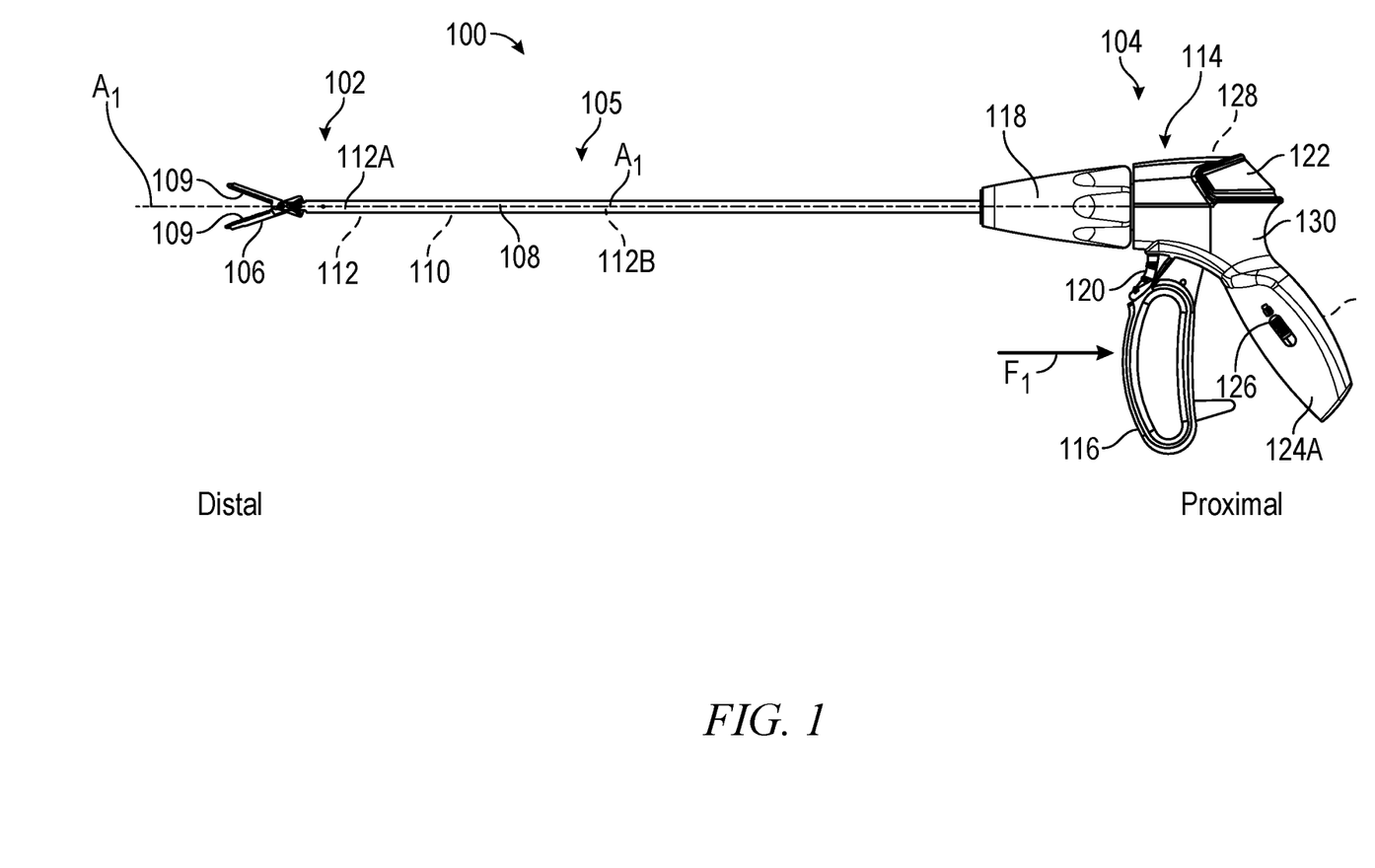
FIG. 1 illustrates a side view of a forceps showing jaws in an open position.

FIG. 1 illustrates a side view of a forceps 100 showing jaws in an open position. The forceps 100 can include an end effector 102, a handpiece 104, and an intermediate portion 105. The end effector 102 can include jaws 106 (including electrodes 109), an outer shaft 108, an inner shaft 110, and a blade assembly 112. The handpiece 104 can include a housing 114, a lever 116, a rotational actuator 118, a trigger 120, an activation button 122, a fixed handle 124a and 124b, and a handle locking mechanism 126. The housing 114 can include a first housing portion 128, and a second housing portion 130. FIG. 1 also shows orientation indicators Proximal and Distal and a longitudinal axis A1.

Generally, the handpiece 104 can be located at a proximal end of the forceps 100 and the end effector 102 can be located at the distal end of the forceps 100. The intermediate portion 105 can extend between the handpiece 104 and the end effector 102 to operably couple the handpiece 104 to the end effector 102. Various movements of the end effector 102 can be controlled by one or more actuation systems of the handpiece 104. For example, the end effector 102 can be rotated along the longitudinal axis A1 of the forceps 100. Also, the handpiece can operate the jaws 106, such as by moving the jaws 106 between open and closed position. The handpiece 104 can also be used to operate the blade assembly 112 for cutting tissue and can operate the electrode 109 for applying electromagnetic energy to tissue. The end effector 102, or a portion of the end effector 102, can be one or more of: opened, closed, rotated, extended, retracted, and electromagnetically energized.

The housing 114 can be a frame that provides structural support between components of the forceps 100. The housing 114 is shown as housing at least a portion of the actuation systems associated with the handpiece 104 for actuating the end effector 102. However, some or all of the actuation components need not be housed within the housing 114 The housing 114 can provide a rigid structure for attachment of components, but the housing 114 does not necessarily house the components completely, or can house a portion of one or more of the components.

The drive shaft 110 can extend through the housing 114 and out of a distal end of the housing 114, or distally beyond housing 114. The jaws 106 can be connected to a distal end of the drive shaft 110. The outer shaft 108 can be a hollow tube positioned around the drive shaft 110. The shafts 108 and 110 can extend along the axis A1. A distal end of the outer shaft 108 can be located adjacent the jaws 106. The distal ends of the drive shaft 110 and the outer shaft 108 can be rotationally locked to the jaws 106. The rotational actuator 118 can be positioned around the distal end of the housing 114. The outer shaft 108 can extend distally beyond the rotational actuator 118. The blade shaft 112b can extend through the drive shaft 110 and the outer shaft 108. A distal end of the blade shaft 112b can be located near the jaws 106. A proximal end of the blade shaft 112b can be within housing 114.

The handpiece 104 can enable a user to extend and retract a blade 112a of the blade assembly 112, which can be attached to a distal end of a blade shaft 112b of the blade assembly 112. In some examples, the blade 112a can extend an entirety of a length between the handle 104 and the end effector 102. In some examples, the handpiece 104 can include features that inhibits the blade assembly 112 from being extended until the jaws 106 are at least partially closed, or fully closed. The blade 112a can be extended by displacing the trigger 120 proximally and the blade 112a can be retracted by allowing the trigger 120 to return distally to a default position.

A proximal portion of the trigger 120 can be connected to the blade shaft 112b within the housing 114 and a distal portion of the trigger 120 can extend outside of the housing 114 adjacent to, and in some examples nested with, the lever 116 in the default or unactuated positions. The activation button 122 can be coupled to the housing 114 and can include or be connected to electronic circuitry within the housing 114. Such circuitry can send or transmit electromagnetic energy through forceps 100 to the jaws 106. In some examples, the electronic circuitry may reside outside the housing 114 but can be operably coupled to the housing 114 and the end effector 102.

In operation of the forceps 100, a user can displace the lever 116 proximally by applying a Force F1 to the lever 116 to actuate the drive shaft 110 to drive the jaws 106 from the open position (FIG. 2A) to the closed position (FIGS. 2B and 2C), which can allow the user to clamp down on and compress a tissue. The handpiece 104 can also allow a user to rotate the rotational actuator 118 to cause the end effector 102 to rotate, such as by rotating both the drive shaft 26 and the outer shaft 28 together.

In some examples, with the tissue compressed, a user can depress the activation button 122 to cause an electromagnetic energy, or in some examples, ultrasound, to be delivered to the end effector 102, such as to the electrode 109 and to the tissue. Application of such energy can be used to seal or otherwise affect the tissue being clamped. In some examples, the electromagnetic energy can cause tissue to be coagulated, sealed, ablated, desiccated or can cause controlled necrosis. When desired, the trigger 120 can be moved to translate the blade assembly 112 distally such that the blade 112a can extend between the jaws 106 in order to cut the tissue within the jaws 106. Such a process can be repeated, as desired.

In some examples, the forceps 100, or other medical device, may not include all the features described or may include additional features and functions, and the operations may be performed in any order. The handpiece 104 can be used with a variety of other end effectors to perform other methods.

Figure 2A:
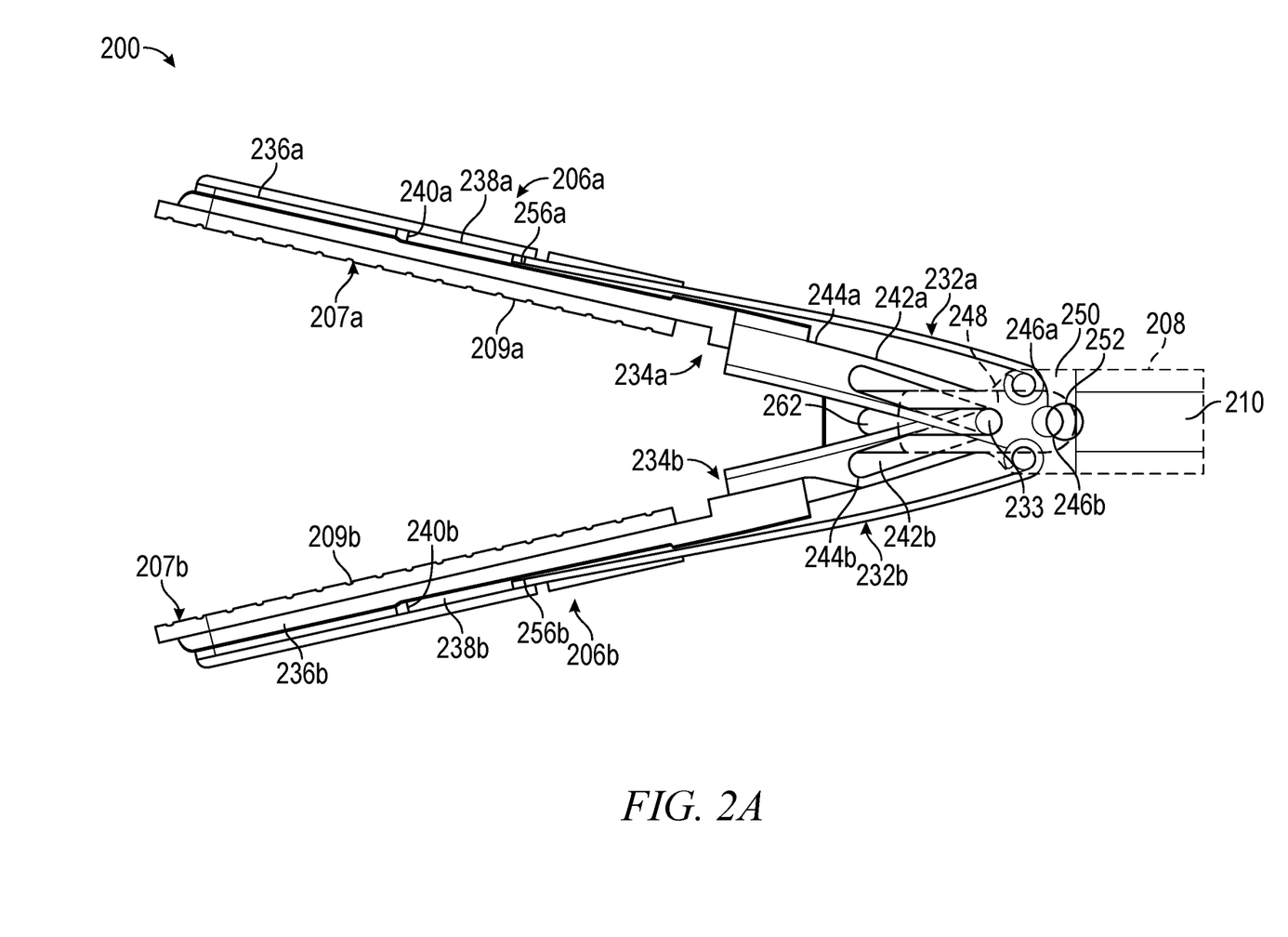
FIG. 2A illustrates a sideview of a portion of forceps in an open position.
Figure 2B:
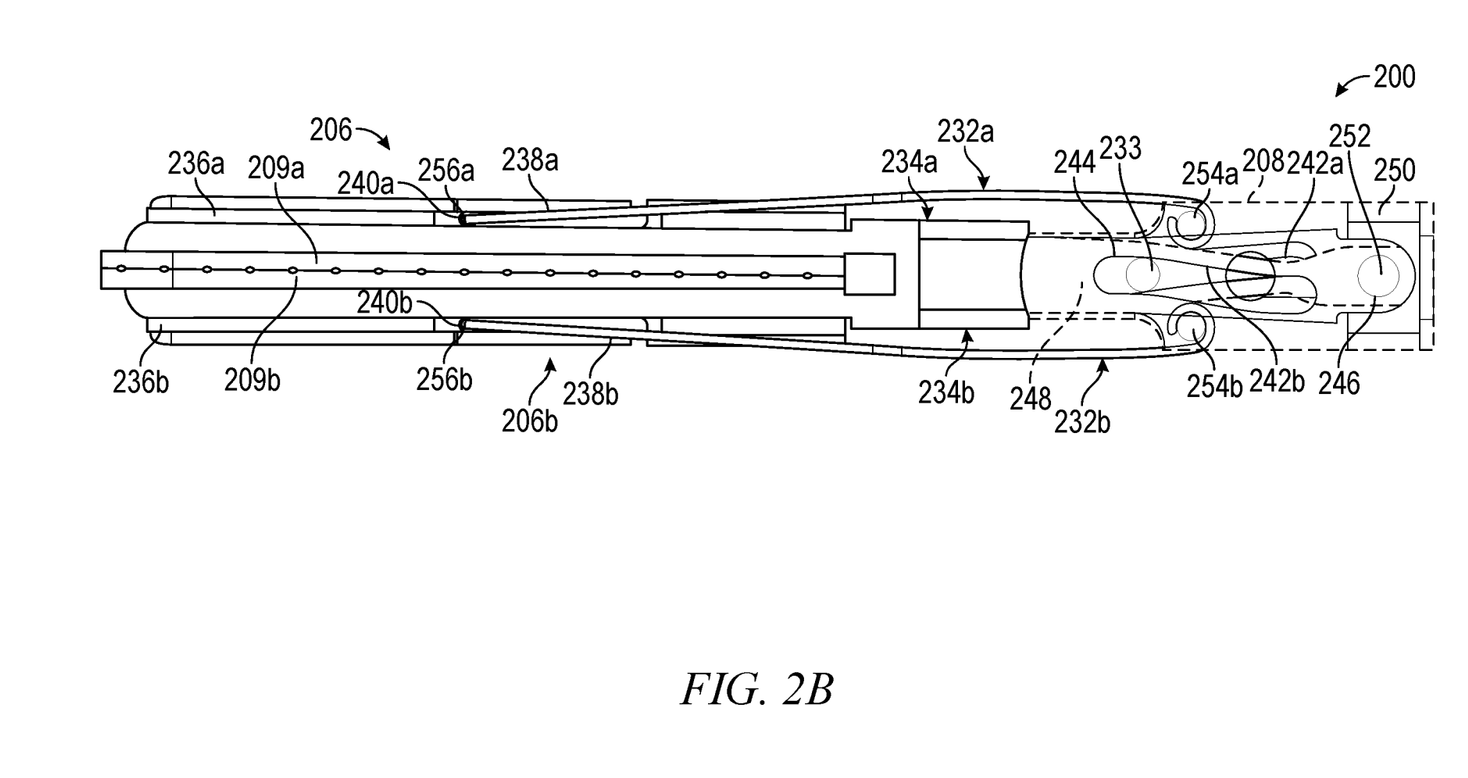
FIG. 2B illustrates a side view of a portion of forceps in a closed position.
Figure 2C:
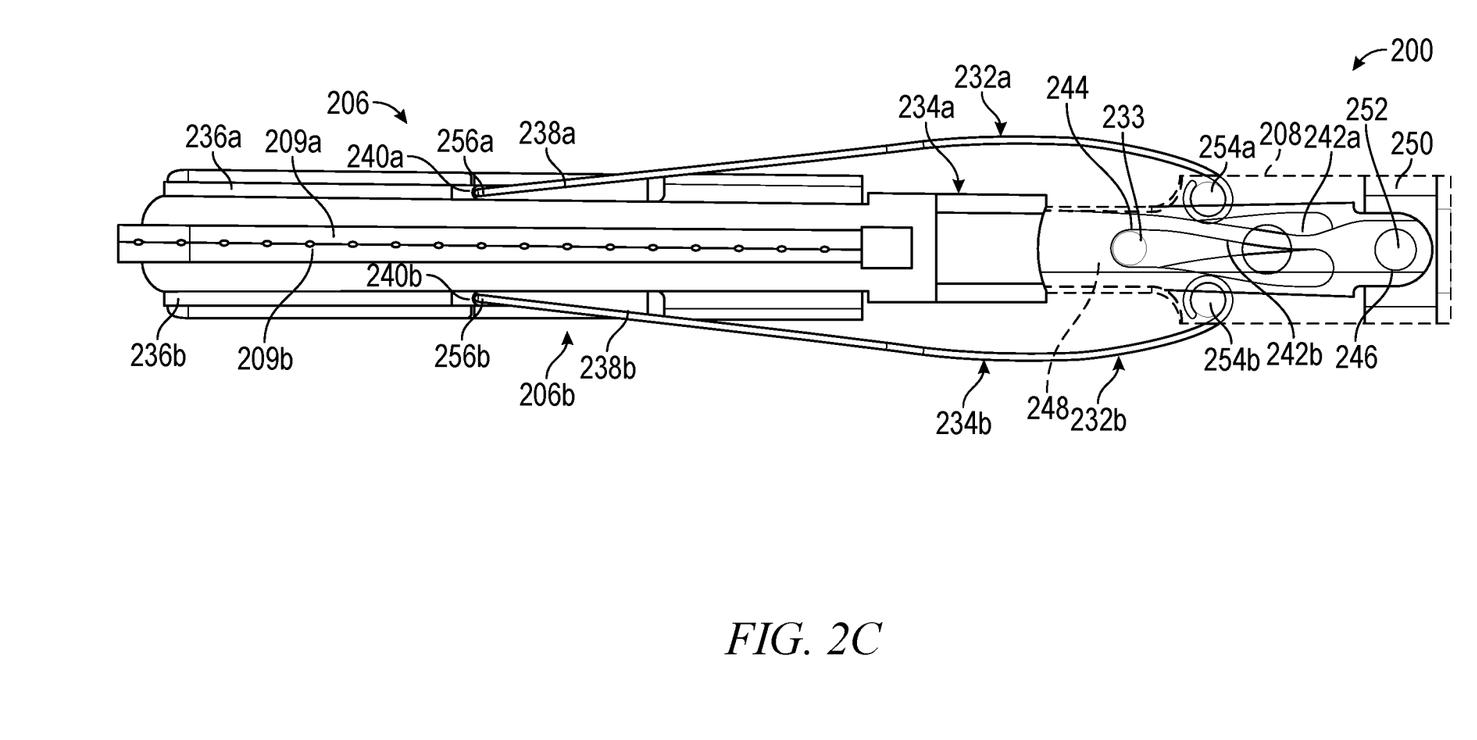
FIG. 2C illustrates a side view of a portion of forceps in a closed position.

FIG. 2A illustrates an isometric view of a portion of forceps 200 in an open position. FIG. 2B illustrates an isometric view of a portion of the forceps 200 in a closed position. FIG. 2C illustrates an isometric view of a portion of the forceps 200 in a closed position. FIGS. 2A-2C are discussed together below.

The forceps 200 can include jaws 206a and 206b, an outer shaft (or first shaft) 208, an inner shaft (or second shaft) 210, actuator arms 232a and 232b, and a cam feature (or cam pin) 233. The first jaw 206a can include a grip plate 207a, an electrode 209a, a frame 234a, and an insulator 236a. The grip plate 207a can define an actuator track 238a including a distal portion 240a. The frame 234a can include a cam interface (or track or slot) 242a including a distal portion 244a and the frame 234a can include a drive connection 246a. Similarly, the second jaw 206b can include a grip plate 207b, an electrode 209b, a frame 234b, and an insulator 236b. The grip plate 207b can define an actuator track 238b including a distal portion 240b. The frame 234b can include a cam interface (or track or slot) 242b including a distal portion 244b and the frame 234b can include a drive connection 246b. The outer shaft 208 can include outer arms 248. The inner shaft 210 can include a head 250, and a connector 252. The forceps can also include arm retainers 254a and 254b.

The forceps 200 can be similar to the forceps 100; additional details are discussed below with respect to the forceps 200. Any of the components of the forceps 200 can be comprised of materials such as one or more of metals, plastics, foams, elastomers, ceramics, composites, combinations thereof, or the like. Materials of some components of the forceps 200 are discussed below in further detail.

The jaws 206a and 206b (collectively referred to as jaws 206) can be rigid or semi-rigid members configured to engage tissue. The jaws 206a and 206b can be coupled to the inner shaft 210, such as pivotably coupled, via the connectors 252. The connectors 252 can be one or more pins, bosses, or the like and can be configured to extend through the drive connections 246a and 246b of the jaws 206a and 206b, respectively, such as when the drive connections 246 are bores extending through the jaw frames 234, to pivotably couple the frames 234 to the first shaft 208. The drive connections 246 can be other tracks, fasteners, or connectors in other examples. In some examples, the jaws 206a and 206b can be pivotably coupled to the outer shaft 210 via one or more pin, boss or connector.

The grip plates 207a and 207b of the jaws 206a and 206b, respectively, can each be a rigid or semi-rigid member configured to engage tissue and/or the opposing jaw to grasp tissue, such as during an electrosurgical procedure. One or more of the grip plates 207a and 207b can include one or more of serrations, projections, ridges, or the like configured to increase engagement pressure and friction between the grip plates 207a and 207b and tissue.

The jaws 206a and 206b can include electrodes 209a and 209b configured to deliver electricity to tissue (optionally through the grip plates 207a and 207b), and optionally through the frames 234a and 234b, respectively. The frame 234a of the upper jaw 206a can extend proximally away from the grip plate 207a, and in some examples, downward when the upper jaw 206a is in the open or partially open positions (as shown in FIG. 2A). Similarly, the frame 234b of the lower jaw 206b can extend proximally away from the grip plate 207b, and in some examples, substantially upward when the upper jaw 206a is in the open position or the partially open position (as shown in FIG. 2A).

The insulators 236a and 236b can be made of electrically insulative material such as one or more of polymers, glasses, rubbers, combinations thereof, or the like. The insulators 236a and 236b can be positioned over the grip plates 207a and 207b and can be connected to the frames 234a and 234b to connected the frames 234a and 234b to the grip plates 207a and 207b, respectively, while electrically isolating the grip plates 207a and 207b from the frames 234a and 234b to help limit electric current from flowing from the electrodes 209a and 209b and the grip plates 207a and 207b to the frames 234a and 234b, which can help prevent electricity from being delivered to incorrect components during coagulation operation (deliver of energy to the electrodes 209) of the forceps 200.

The actuator arms 232a and 232b can be flexible or semi-rigid members connected to the outer shaft 208 via the arm retainers 254a and 254b at a proximal portion of the actuator arms 232a and 232b, respectively. The actuator arms 232 can be made of resilient materials such as spring steel, Nickel Titanium (Nitinol), or the like such that the actuator arms 232 can be configured to elastically bend or flex such as being configured to bow laterally outward with respect to the jaws 206. In some examples, the actuator arms 232a and 232b can be made of non-spring (or reduced spring) materials, such as one or more of polymer, steel, aluminum, titanium, or the like.

Distal portions 256a and 256b of the actuator arms 232a and 232b can be positioned in the actuator tracks 238a and 238b, respectively, and the actuator tracks 238 can be translatable or movable relative to the arms 232, as discussed in further detail below. The arm retainers 254 can be pins, screws, bosses, or other fasteners configured to connect the actuator arms 232 to the shaft. In some examples, the arm 232a can be connected to the retainer 254a at a top portion (or laterally outer portion) of the outer shaft 208 and the arm 232b can be connected to the retainer 254b at a bottom portion (or laterally outer portion opposite the retainer 254a) of the outer shaft 208, which can help provide clearance for components, such as a blade, to pass between the retainers 254.

The grip plate 207a, such as a top, superior, or laterally outer portion of the grip plate 207a, can define the actuator track 238a. Similarly, the grip plate 207b, such as a top, superior, or laterally outer portion can define the actuator track 238b. The actuator tracks 238a and 238b can be similar but orientated in opposite directions. In other examples, the actuator tracks 238a and 238b can be the same. The actuator track 238a can extend along a top portion of the grip plate 207a and can include a distal portion 240a which can define a distal termination of the actuator track 238a. A proximal portion can similarly define a proximal termination of the actuator track 238a. In some examples, the proximal portion of the actuator track 238a can be open. The actuator track 238a can be configured to receive and retain a portion of the actuator arm 232a therein. During operation, the distal portion 256a of the actuator arm 232a can be configured to engage a distal portion 240a of the actuator track 238a, as discussed in further detail below. The actuator track 238b can be similarly configured to the actuator track 238a.

The outer shaft 208, which can be similar to the shaft 108 discussed above, can include the outer arms 248, that can extend distally and can have a height that is smaller than a diameter of the outer shaft 208. The outer arms 248 can be connected to the cam feature 233, which can extend between the outer arms 248. The cam feature 233 can be a pin, boss, bosses, or other projection or protuberance. In some examples, the cam feature 233 can be a track and a boss or pins can extend from the frames 234a and 234b into cam features 233 of the outer arms 248.

In examples where the cam feature 233 is a pin or bosses it can extend from the outer arms 248 and can extend into or through the cam interfaces 242a and 242b of the frames 234a and 234b of the jaws 206a and 206b, respectively. The cam interfaces 242 can be tracks or slots in some examples and can be movable along the cam feature 233.

The inner shaft 210 can be positioned within the outer shaft 208 and can be configured to translate (or move) substantially proximally and distally therein. The head 250 can be located at a distal portion of the inner shaft 210 and can have a relatively larger diameter such as to help limit non-translational movement (e.g., lateral movement) of the inner shaft 210 with respect to the outer shaft 208. The connector 252 (or connectors 252) can be connected to the head 250 and can be connected to the frames 234a and 234b via the drive connections 246a and 246b of the frames 234a and 234b, respectively.

In operation of some examples, the forceps can be in an open position where a proximal portion of the cam interfaces 242a and 242b are engaged with the cam feature 233 such that the jaws 206a and 206b are in the open position, as shown in FIG. 2A. Prior to closing, the jaws 206a and 206b can be in partially open or partially closed positions between the positions shown in FIGS. 2A and 2B. In such a position, the inner shaft 210 can be in a distal position relative to the outer shaft 208 (or distal of a proximal-most position).

In some examples, one jaw, such as the jaw 206b, can be fixed with respect to the outer shaft 208. In such an example, only the jaw 206a may move and a partially open position can be a position where the jaw 206a moves away from the jaw 206b and an open position can be where the jaw 206a is limited from opening further such as via contact between the cam interface 242a and the cam feature 233. Closing of the jaw 206a in a single acting configuration can include movement of the jaw 206a with respect to the outer shaft 210 and with respect to the jaw 206b. That is, in some examples, one of the jaws 206 (such as the jaw 206b) can be fixed with respect to one of the inner shaft 210 and the outer shaft 208, where the other jaw (206a) can be movable with respect to the inner shaft 210, the outer shaft 208, and the jaw 206b.

In a dual-acting configuration, when it is desired to close the jaws 206, a handle (such as the lever 116) can be operated to cause the inner shaft 210 and the head 250 to move proximally, causing the frames 234a and 234b to move proximally. When the frames 234 move proximally, the cam interfaces 242a and 242b can move along the cam feature 233 to cause the frames 234a and 234b to move towards each other and therefore to cause the grip plates 207 to move towards each other. As the inner shaft 210 pulls the frames 234a and 234b proximally, the actuator tracks 238a and 238b can move proximally with respect to the arms 232a and 232b, respectively, such that the distal portions 240a and 240b of the actuator tracks 238a and 238b can move towards the distal portions 256a and 256b of the arms 232a and 232b, respectively. When the grip plates 207a and 207b contact each other the grip plate 207a can apply a force (or a closing or clamping force) on the grip plate 207b and the grip plate 207b can apply a force on the grip plate 207b.

During continued movement of the inner shaft 210, the grip plates 207a and 207b can contact each other, as shown in FIG. 2B. The cam feature 233 can be positioned near, but not necessarily at, the distal portions 244 of the cam guides 242. The inner shaft 210 can be moved further proximally if desired. Such movement can cause the camming feature 233 to move into the distal portions 244 where the distal portions 244 may or may not cause further movement of the frames 234 and the grip plates 207. Such movement of the frames 234 can also cause the distal portions 240a and 240b of the actuator tracks 238a and 238b to move proximally towards the distal portions 256a and 256b of the actuator arms 232a and 232b to eventually engage the distal portions 256a and 256b, where the cam feature 233 can be still spaced away from a termination of the distal portions 244 of the cam guides 242.

Because the actuator arms 232*a* and 232*b* are fixed to the outer shaft 208, when the distal portions 256*a* and 256*b* of the actuator arms 232*a* and 232*b* engage the distal portions 240 of the actuator tracks 238*a* and 238*b*, respectively, and because the cam feature 233 can be still spaced away from a termination of the distal portions 244 of the cam guides 242 (as shown in FIG. 2B), force applied by continuing proximal movement of the inner shaft 208 with respect to the outer shaft 210 can be applied or transferred from the distal portions 240 of the actuator tracks 238 to the distal portions 256*a* and 256*b* of the actuator arms 232*a* and 232*b*. And, because the actuator arms 232*a* and 232*b* can be resilient members, the force applied by the distal portions 240 of the actuator tracks 238 can cause the actuator arms 232*a* and 232*b* to flex or bend (as shown in FIG. 2C), effectively causing, for example, a medial or middle portion of the actuator arms 232*a* and 232*b* to bow outward (e.g., laterally). This movement or flex of the actuator arms 232*a* and 232*b* can be elastic deformation of the actuator arms 232*a* and 232*b* and can result in a force directed laterally inward and applied from the actuator arm 232*a* to the grip plate 207*a* to help increase the closing force applied by the grip plate 207*a* to the grip plate 207*b*. Similarly, actuator arm 232*b* can apply a force on the grip plate 207*b* to help increase the closing force applied by the grip plate 207*b* to the grip plate 207*a*. The actuator arms 232*a* and 232*b* can thereby increase the closing force applied by the grip plates 207*a* and 207*b* to each other (and to anything between the grip plates, such as tissue).

In some examples, a location of the distal portions 240 of the actuator tracks 238 can be more than halfway past a distal to proximal midpoint of the grip plates 207, which can help to increase a closing force at distal portions of the grip plates 207.

In another example, the outer shaft 208 can be moved with respect to the inner shaft 210, which can allow a position of the jaws 206 to remain fixed with respect to the handpiece 104. More specifically, when it is desired to close the jaws 206, a handle (such as the lever 116) can be operated to cause the outer shaft 208 to move distally, causing the camming feature 233 to move distally. When the camming feature 233 moves distally, the cam interfaces 242*a* and 242*b* can move along the cam feature 233 to cause the frames 234*a* and 234*b* to move towards each other and therefore to cause the grip plates 207 to move towards each other. As the outer shaft 208 moves distally, the outer shaft can move the arms 232*a* and 232*b* distally with respect to the actuator tracks 238*a* and 238*b*, such that the distal portions 256*a* and 256*b* of the arms 232*a* and 232*b* can move towards the distal portions 240*a* and 240*b* of the actuator tracks 238*a* and 238*b*, respectively. When the grip plates 207*a* and 207*b* contact each other the grip plate 207*a* can apply a force (or a closing or clamping force) on the grip plate 207*b* and the grip plate 207*b* can apply a force on the grip plate 207*b*.

During continued movement of the outer shaft 208, the grip plates 207*a* and 207*b* can be in contact with each other. The cam feature 233 can be positioned near, but not necessarily at, the distal portions 244 of the cam guides 242. The outer shaft 208 can be moved further distally, if desired. Such movement can cause the camming feature 233 to move into the distal portions 244 where the distal portions 244 may or may not cause further movement of the arms 232 and the grip plates 207. When the arms 232 move further distally, the distal portions distal portions 256*a* and 256*b* of the actuator arms 232*a* and 232*b* can continue to move distally toward the distal portions 240*a* and 240*b* of the actuator tracks 238*a* and 238*b* to eventually engage the distal portions 256*a* and 256*b*, where the cam feature 233 can be still spaced away from a termination of the distal portions 244 of the cam guides 242.

Because the actuator arms 232*a* and 232*b* are fixed to the outer shaft 208, when the distal portions 256*a* and 256*b* of the actuator arms 232*a* and 232*b* engage the distal portions 240 of the actuator tracks 238*a* and 238*b*, respectively, and because the cam feature 233 can be still spaced away from a termination of the distal portions 244 of the cam guides 242, force applied by continuing distal movement of the outer shaft 210 with respect to the inner shaft 208 can be applied or transferred from the distal portions 256*a* and 256*b* to the distal portions 240 of the actuator tracks 238. And, because the actuator arms 232*a* and 232*b* can be resilient members, the force applied can cause the actuator arms 232*a* and 232*b* to flex or bend, effectively causing, for example, a medial or middle portion of the actuator arms 232*a* and 232*b* to bow outward (e.g., laterally). This movement or flex of the actuator arms 232*a* and 232*b* can be elastic deformation of the actuator arms 232*a* and 232*b* and can result in a force directed laterally (e.g., inward) and applied from the actuator arm 232*a* to the grip plate 207*a* to help increase the closing force applied by the grip plate 207*a* to the grip plate 207*b*. Similarly, actuator arm 232*b* can apply a force on the grip plate 207*b* to help increase the closing force applied by the grip plate 207*b* to the grip plate 207*a*. The actuator arms 232*a* and 232*b* can thereby increase the closing force applied by the grip plates 207*a* and 207*b* to each other (and to anything between the grip plates, such as tissue).

As discussed above, either of the shafts 208 and 210 can be moved relative to the other shaft and to the handpiece 104 to operate the jaws 206 and the arms 232 to close the jaws 206 and apply a closing force to the jaws 206 by the arms 232.

In some examples, the actuator arms 232 can be configured to apply a force on the jaws 206 when the jaws move out of the open position (as shown in FIG. 2A).

Figure 3:
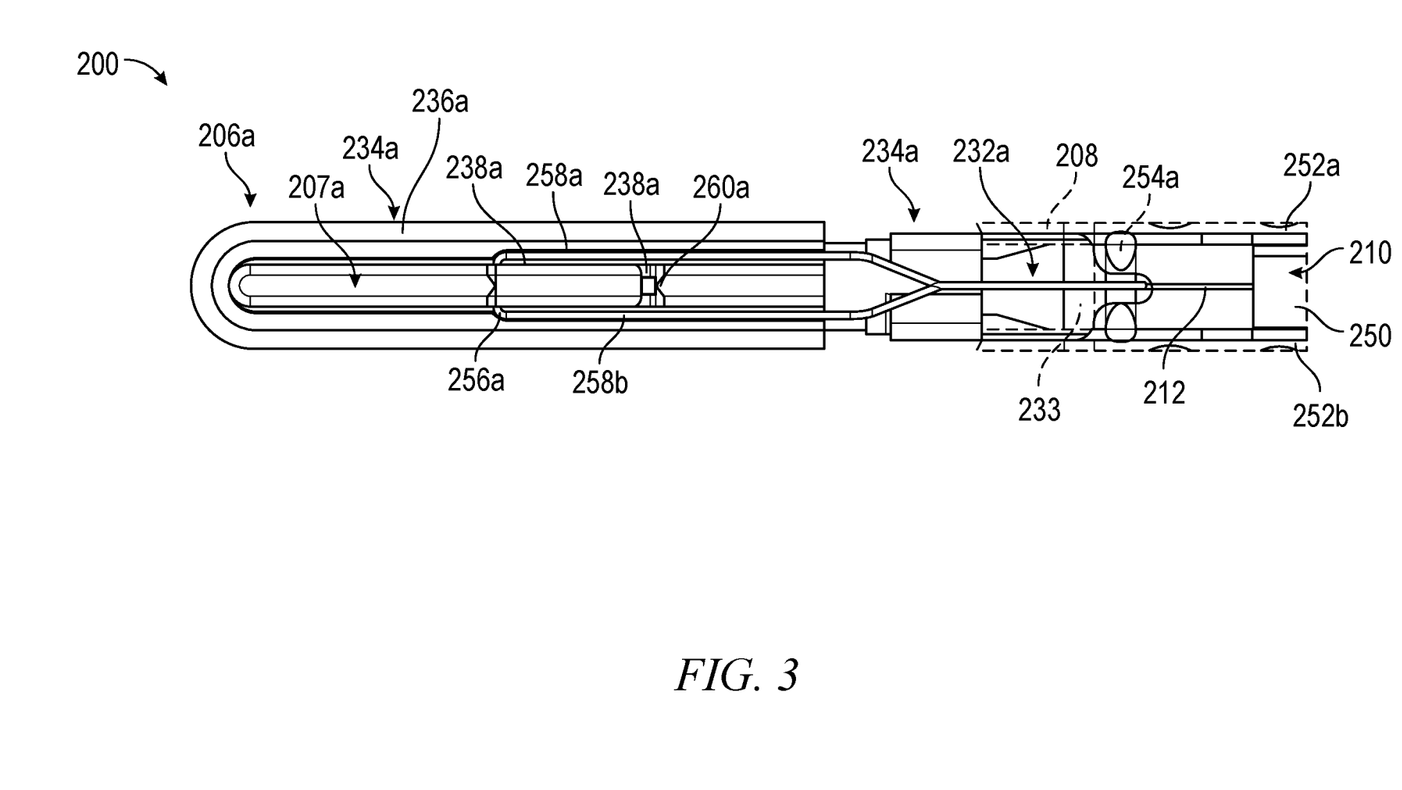
FIG. 3 illustrates a top view of a portion of forceps in a closed position.

FIG. 3 illustrates an isometric view of a portion of the forceps 200 in a closed position. The forceps 200 of FIG. 3 can be consistent with the forceps of FIGS. 1-2B discussed above. Additional details of the forceps are shown in FIG. 3.

For example, FIG. 3 shows that the actuator arm 232*a* can include a first arm 258*a* and a second arm 258*b* which can be connected to the distal portion 256*a*. FIG. 3 also shows that the actuator track 238*a* can include an opening 260*a*. The opening 260*a* can be configured to receive the distal portion 256*a* therein and the arms 258*a* and 258*b* can be positioned laterally outward of the track 238*a* such that movement of the track 238*a* with respect to the arm 232*a* is guided by the distal portion 256*a*.

The opening 260*a* of the actuator track 238*a* can be positioned such that the distal portion 240*a* is proximal of the distal portion 256*a* of the actuator arm 232*a* when the jaws 206 are in the fully open position (as shown in FIG. 2A) to help prevent the distal portion 256*a* from escaping the actuator track 238*a* during operation while also providing an opening for inserting the distal portion 256*a* into the actuator track 238*a* during assembly of the forceps 200. The actuator arm 232*b* and the jaw 206*b* can be similarly configured to the actuator arm 232*a* and the jaw 206*a*.

FIG. 3 also shows that the blade 212 can extend through the internal shaft 210 and the external shaft 208. The blade 212 can also extend between the retainers 254*a* and 254*b*. Also, the blade 212 can include a slot 262 (shown in FIG. 2A) that allows the cam feature 233 (and optionally the connector 252) to extend through the blade 212. In other examples, the cam feature 233 can be multiple bosses or projections such that the slot 262 of the blade 212 can be omitted.

Figure 4:
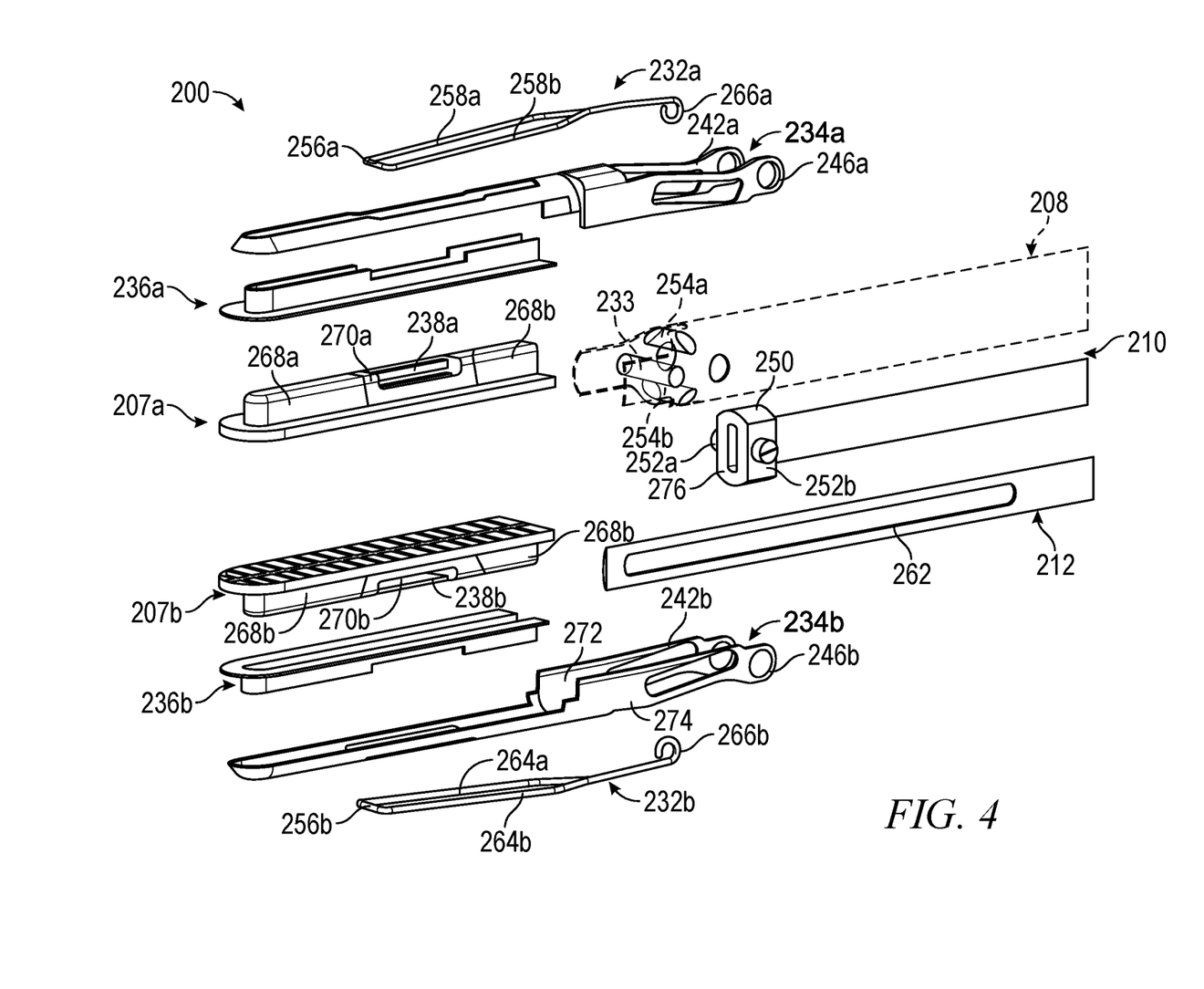
FIG. 4 illustrates an exploded isometric view of a forceps.

FIG. 4 illustrates an exploded isometric view of the forceps 200. The forceps 200 of FIG. 4 can be consistent with the forceps of FIGS. 1-3 discussed above. Additional details of the forceps are shown in FIG. 4.

For example, FIG. 4 shows arm connectors 266a and 266b of the actuator arms 232a and 232b, respectively. The connectors 266 can be curved or rounded portions of the arms 232 configured to receive and retain at least a portion of the arm retainers 254a and 254b, respectively, to secure the actuator arms 232a and 232b to the outer shaft 208.

FIG. 4 also shows that the grip plates 207a and 207b can include a conductive portion 268a and 268b, respectively, and an insulative portion 270a and 270b. The conductive portions 268a and 268b can be connected to the insulative portions 270a and 270b, respectively. The conductive portions 268 can be made of electrically conductive materials such as one or more of copper, silver, aluminum, or the like. The insulative portions 270 can be made of less conductive, or electrically insulative materials such as one or more of polymer, glass, rubber, ceramic, or the like. Because the insulative portions 270 are connected to the actuator arms 232, the insulative portions 270 can help prevent electricity from flowing from the electrodes 209 to the grip plates 207 to the conductive portions 268 to the actuator arms 232 and to the outer shaft 208, which could cause a short circuit for the electrodes 209.

FIG. 4 also shows that the frame 234b can include a first member 272 and a second member 274 which can be substantially parallel and can be spaced from each other. Each member can include the cam interface 242b and the drive connection 246b. In some examples, the members of the frame 234a can be wider (laterally) than the members of the frame 234b. In some examples, the members of the frames 234 can have similar or the same widths but the members can be interlaced or offset. In some examples, the frames 234 can include only one member. FIG. 4 also shows that the head 250 of the inner shaft 210 can include a blade passage 276 for guiding a blade through the inner shaft 210.

NOTES AND EXAMPLES

The following, non-limiting examples, detail certain aspects of the present subject matter to solve the challenges and provide the benefits discussed herein, among others.

Example 1 is a surgical forceps comprising: a first shaft extending longitudinally; a cam feature connected to the first shaft; a first jaw defining a cam interface and an actuator track, the cam interface engaged with the cam feature, and the first jaw movable between an open position and a closed position; a second jaw engaged with the first shaft and opposing the first jaw, the first jaw movable relative to the second jaw; an actuator arm including: a proximal portion connected to the first shaft; and a distal portion located at least partially in the actuator track of the first jaw and configured to apply a closing force on the first jaw when the first jaw is moved out of the open position; and a second shaft connected to the first jaw, the second shaft translatable relative to the first shaft to move the cam feature along the cam interface of the first jaw to move the first jaw between the open position and the closed position, and translatable to move the actuator arm relative to the actuation track between a proximal position and a distal position, the actuator arm configured to increase the closing force as the actuator arm is moved from the proximal position to the closed position.

In Example 2, the subject matter of Example 1 optionally includes wherein the cam interface includes a distal portion configured to receive the cam feature therein when the second shaft moves proximal of the proximal position.

In Example 3, the subject matter of Example 2 optionally includes wherein the distal portion of the actuator arm is configured to engage the actuator track to limit distal movement of the actuator arm relative to the actuation track and the first jaw.

In Example 4, the subject matter of Example 3 optionally includes wherein the actuator arm is configured to increase the closing force applied to by the first jaw when the distal portion of the actuator arm engages the actuator track and when the cam feature is in the distal portion of the cam interface.

In Example 5, the subject matter of Example 4 optionally includes wherein the actuator arm is configured to flex to apply the closing force to the second jaw.

In Example 6, the subject matter of Example 5 optionally includes wherein the actuator arm is a biasing element.

In Example 7, the subject matter of any one or more of Examples 5-6 optionally include wherein the actuator arm is made of spring steel.

In Example 8, the subject matter of any one or more of Examples 1-7 optionally include wherein the cam interface is a first cam interface and the actuator track is a first actuator track, wherein the second jaw defines a second cam interface and a second actuator track, wherein the cam feature is engaged with the first cam interface and the second cam interface, and wherein the second shaft is connected to the first jaw and the second jaw and is configured to move the cam feature along the first cam interface and the second cam interface to move the first jaw and to move the second jaw with respect to the first shaft between open and closed positions.

In Example 9, the subject matter of Example 8 optionally includes a second actuator arm including: a second proximal portion connected to the first shaft; and a second distal portion located at least partially in the second actuator track of the second jaw and configured to apply a second closing force on the second jaw when the second jaw is moved out of the open position.

In Example 10, the subject matter of any one or more of Examples 1-9 optionally include wherein the cam feature is a cam pin and wherein the cam interface is a cam track.

Example 11 is a surgical forceps comprising: a first shaft extending longitudinally; a cam pin; a first jaw engaged with the first shaft and defining a cam track and an actuator track, the cam track engaged with the cam pin, and the first jaw movable between an open position and a closed position; a second jaw engaged with the first shaft and opposing the first jaw; an actuator arm including: a proximal portion; and a distal portion located at least partially in the actuator track of the first jaw and configured to apply a closing force on the first jaw when the first jaw is moved out of the open position; and a second shaft translatable relative to the first shaft to cause relative movement of the cam track of the first jaw with respect to and along the cam pin to move the first jaw between the open position and the closed position, and the second shaft translatable to move the actuation track relative to the actuator arm to cause engagement between the actuation track and the actuator arm to increase the closing force.

In Example 12, the subject matter of Example 11 optionally includes wherein the cam track includes a distal portion configured to receive the cam pin therein.

In Example 13, the subject matter of Example 12 optionally includes wherein the distal portion of the actuator arm is configured to engage the actuator track to limit proximal movement of the actuator track relative to the actuator arm and the first jaw.

In Example 14, the subject matter of Example 13 optionally includes wherein the actuator arm is configured to increase the closing force applied to by the first jaw when the distal portion of the actuator arm engages the actuator track and when the cam feature is in the distal portion of the cam interface.

In Example 15, the subject matter of Example 14 optionally includes wherein the actuator arm is configured to flex to apply the closing force to the second jaw.

Example 16 is a surgical forceps comprising: a first shaft extending longitudinally; a cam feature connected to the first shaft; a first jaw defining a first cam interface and a first actuator track, the first cam interface engaged with the cam feature; a second jaw defining a second cam interface and a second actuator track, the second cam interface engaged with the second cam feature, and the first jaw and the second jaw movable relative to the first shaft between an open position and a closed position; first and second actuator arms including: a proximal portion connected to the first shaft; and a distal portion located at least partially in the actuator track of the first jaw and the second jaw, respectively, and configured to apply a closing force on the first jaw and the second jaw, respectively, when the first jaw and the second jaw are moved out of the open position; and a second shaft connected to the first jaw and the second jaw, the second shaft translatable relative to the first shaft to move the first cam interface of the first jaw and the second cam interface of the second jaw along the cam feature to move the first jaw and the second jaw between the open position and the closed position.

In Example 17, the subject matter of Example 16 optionally includes wherein the second shaft is translatable to move the actuation track relative to the first actuator arm and the second actuator arm between proximal positions and distal positions, the first actuator arm configured to increase the closing force as the first actuation track is moved from the distal position to the proximal position.

In Example 18, the subject matter of Example 17 optionally includes wherein the second actuator arm is configured to increase the closing force as the second actuation track is moved from the distal position to the proximal position.

In Example 19, the subject matter of any one or more of Examples 16-18 optionally include wherein the distal portions of the first actuator arm and the second actuator arm are configured to engage the first actuator track and the second actuator track, respectively, to limit proximal movement of the first actuator track and the second actuator track relative to the first actuator arm and the first jaw and the second actuator arm and the second jaw, respectively.

In Example 20, the subject matter of Example 19 optionally includes wherein the first actuator arm and the second actuator arm are configured to increase the closing force applied to by the first jaw and the second jaw, respectively, when the distal portions of the first actuator arm and the second actuator arm engage the first actuator track and the second actuator track, respectively, and when the cam feature is in the distal portions of the first cam interface and the second cam interface.

In Example 21, the apparatuses or method of any one or any combination of Examples 1-20 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A surgical forceps comprising:
a first shaft extending longitudinally;
a cam feature connected to the first shaft;
a first jaw defining a cam interface and an actuator track, the cam interface engaged with the cam feature, and the first jaw movable between an open position and a closed position;
a second jaw engaged with the first shaft and opposing the first jaw, the first jaw movable relative to the second jaw;
an actuator arm including:
a proximal portion connected to the first shaft; and a distal portion located at least partially in the actuator track of the first jaw and configured to apply a closing force on the first jaw when the first jaw is moved out of the open position; and a second shaft connected to the first jaw, the second shaft translatable relative to the first shaft to move the cam feature along the cam interface of the first jaw to move the first jaw between the open position and the closed position, and translatable between a proximal position and a distal position to move the actuator arm relative to the actuator track between a proximal position and a distal position, the actuator arm configured to increase the closing force as the actuator arm is moved from the proximal position of the actuator arm to the distal position of the actuator arm;

wherein the cam interface includes a distal portion configured to receive the cam feature therein when the second shaft moves proximal of the proximal position of the second shaft.

2. The surgical forceps of claim 1, wherein the distal portion of the actuator arm is configured to translate along the actuator track and engage the actuator track to limit distal movement of the actuator arm relative to the actuator track and the first jaw.

3. The surgical forceps of claim 2, wherein the actuator arm is configured to increase the closing force applied to by the first jaw when the distal portion of the actuator arm engages the actuator track and when the cam feature is in the distal portion of the cam interface.

4. The surgical forceps of claim 3, wherein the actuator arm is configured to flex to apply the closing force to the second jaw.

5. The surgical forceps of claim 4, wherein the actuator arm is a biasing element.

6. The surgical forceps of claim 4, wherein the actuator arm is made of spring steel.

7. The surgical forceps of claim 1, wherein the cam interface is a first cam interface and the actuator track is a first actuator track, wherein the second jaw defines a second cam interface and a second actuator track, wherein the cam feature is engaged with the first cam interface and the second cam interface, and wherein the second shaft is connected to the first jaw and the second jaw and is configured to move the cam feature along the first cam interface and the second cam interface to move the first jaw and to move the second jaw with respect to the first shaft between open and closed positions.

8. The surgical forceps of claim 7, further comprising:
a second actuator arm including:
 a second proximal portion connected to the first shaft; and
 a second distal portion located at least partially in the second actuator track of the second jaw and configured to apply a second closing force on the second jaw when the second jaw is moved out of the open position.

9. The surgical forceps of claim 1, wherein the cam feature is a cam pin and wherein the cam interface is a cam track.

10. A surgical forceps comprising:
a first shaft extending longitudinally;
a cam pin;
a first jaw engaged with the first shaft and defining a cam track and an actuator track, the cam track engaged with the cam pin, and the first jaw movable between an open position and a closed position;

a second jaw engaged with the first shaft and opposing the first jaw;
an actuator arm including:
 a proximal portion; and
 a distal portion located at least partially in the actuator track of the first jaw and configured to apply a closing force on the first jaw when the first jaw is moved out of the open position; and
a second shaft translatable relative to the first shaft to cause relative movement of the cam track of the first jaw with respect to and along the cam pin to move the first jaw between the open position and the closed position, and the second shaft translatable between a proximal position and a distal position to move the actuator track relative to the actuator arm to cause engagement between the actuator track and the actuator arm to increase the closing force;
wherein the cam track includes a distal portion configured to receive the cam feature therein when the second shaft moves proximal of the proximal position.

11. The surgical forceps of claim 10, wherein the cam track includes a distal portion configured to receive the cam pin therein.

12. The surgical forceps of claim 11, wherein the distal portion of the actuator arm is configured to engage the actuator track to limit proximal movement of the actuator track relative to the actuator arm and the first jaw.

13. The surgical forceps of claim 12, wherein the actuator arm is configured to increase the closing force applied to by the first jaw when the distal portion of the actuator arm engages the actuator track and when the cam pin is in the distal portion of the cam track.

14. The surgical forceps of claim 13, wherein the actuator arm is configured to flex to apply the closing force to the second jaw.

15. A surgical forceps comprising:
a first shaft extending longitudinally;
a first cam feature and a second cam feature connected to the first shaft;
a first jaw defining a first cam interface and a first actuator track, the first cam interface engaged with the cam feature;
a second jaw defining a second cam interface and a second actuator track, the second cam interface engaged with the second cam feature, and the first jaw and the second jaw movable relative to the first shaft between an open position and a closed position;
first and second actuator arms including:
 a proximal portion connected to the first shaft; and
 a distal portion located at least partially in respective ones of the actuator track of the first jaw and the second jaw, respectively, and configured to apply a closing force on the first jaw and the second jaw, respectively, when the first jaw and the second jaw are moved out of the open position; and
a second shaft connected to the first jaw and the second jaw, the second shaft translatable relative to the first shaft between a proximal position and a distal position to move the first cam interface of the first jaw and the second cam interface of the second jaw along the cam feature to move the first jaw and the second jaw between the open position and the closed position;
wherein the first cam interface and the second cam interface each include a distal portion configured to receive the cam feature therein when the second shaft moves proximal of the proximal position of the second shaft.

16. The surgical forceps of claim 15, wherein the second shaft is translatable to move the actuation track relative to the first actuator arm and the second actuator arm between proximal positions and distal positions, the first actuator arm configured to increase the closing force as the first actuation track is moved from the distal position to the proximal position.

17. The surgical forceps of claim 16, wherein the second actuator arm is configured to increase the closing force as the second actuation track is moved from the distal position to the proximal position.

18. The surgical forceps of claim 15, wherein the distal portions of the first actuator arm and the second actuator arm are configured to engage the first actuator track and the second actuator track, respectively, to limit proximal movement of the first actuator track and the second actuator track relative to the first actuator arm and the first jaw and the second actuator arm and the second jaw, respectively.

19. The surgical forceps of claim 18, wherein the first actuator arm and the second actuator arm are configured to increase the closing force applied to by the first jaw and the second jaw, respectively, when the distal portions of the first actuator arm and the second actuator arm engage the first actuator track and the second actuator track, respectively, and when the cam feature is in the distal portions of the first cam interface and the second cam interface.

* * * * *